US010195407B2

United States Patent
Vadivelu et al.

(10) Patent No.: US 10,195,407 B2
(45) Date of Patent: Feb. 5, 2019

(54) CRANIAL PLATE FOR ULTRASOUND GUIDED CEREBRAL SHUNT PLACEMENT

(71) Applicant: Children's Hospital Medical Center, Cincinnati, OH (US)

(72) Inventors: Sudhakar Vadivelu, Mason, OH (US); Kelsey Radabaugh, Dayton, OH (US); Heather Smith, Dayton, OH (US); Michael Woeste, Dayton, OH (US); Brandon Heckman, Dayton, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 447 days.

(21) Appl. No.: 15/043,415

(22) Filed: Feb. 12, 2016

(65) Prior Publication Data
US 2016/0263361 A1 Sep. 15, 2016

Related U.S. Application Data

(60) Provisional application No. 62/131,888, filed on Mar. 12, 2015.

(51) Int. Cl.
*A61M 27/00* (2006.01)
*A61M 25/02* (2006.01)
*A61B 17/70* (2006.01)
*A61B 17/80* (2006.01)
*A61B 17/68* (2006.01)

(52) U.S. Cl.
CPC .......... *A61M 27/006* (2013.01); *A61M 25/02* (2013.01); *A61B 17/688* (2013.01); *A61B 17/7055* (2013.01); *A61B 17/8061* (2013.01); *A61B 17/8085* (2013.01); *A61M 2025/0213* (2013.01)

(58) Field of Classification Search
CPC ........ A61M 27/006; A61M 2025/0213; A61M 25/02
See application file for complete search history.

(56) References Cited

U.S. PATENT DOCUMENTS

2005/0182420 A1* 8/2005 Schulte ................ A61N 1/0539
606/130
2009/0112327 A1* 4/2009 Lane .................... A61N 1/0539
623/17.19
2014/0073859 A1* 3/2014 Schorn ................ A61B 17/3468
600/300

OTHER PUBLICATIONS

Whitehead et al., "No Significant Improvements in the Rate of Accurate Ventricular Catheter Location Using Ultrasound-guided CSF Shunt Insertion: A Prospective, Controlled Study by the Hydrocerphalus Clinical Research Network." *Journal of Neurosurgery: Pediatrics*: 565-74, Dec. 2013.

(Continued)

*Primary Examiner* — Leslie Deak
(74) *Attorney, Agent, or Firm* — Faegre Baker Daniels LLP

(57) ABSTRACT

A ventricular catheter assembly including a proximal catheter and a cooperating cranial cover. The cranial cover includes a base plate having an opening aligned with a burr hole in the skull of a person. A guide extends upwardly from the base plate and receives the proximal catheter.

8 Claims, 8 Drawing Sheets

(56) References Cited

OTHER PUBLICATIONS

Kestle et al., "A Standardized Protocol to Reduce Cerebrospinal Fluid Shunt Infection: The Hydrocephalus Clinical Research Network Quality Improvement Initiative." *Journal of Neurosurgery: Pediatrics*: 22-29, Jul. 2011.

Crowley et al., "Intraoperative Ultrasound Guidance for the Placement of Permanent Ventricular Cerebrospinal Fluid Shunt Catheters: A Single-Center Historical Cohort Study." *World Neurosurgery*: 397-403, Feb. 2014.

\* cited by examiner

CRANIAL PLATE FOR ULTRASOUND GUIDED CEREBRAL SHUNT PLACEMENT

CROSS-REFERENCE TO RELATED APPLICATION

The present application claims priority to U.S. Provisional Patent Application Ser. No. 62/131,888, filed Mar. 12, 2015, the disclosure of which is expressly incorporated herein by reference.

BACKGROUND AND SUMMARY

The present invention relates generally to a system and method for cerebral shunt placement and, more particularly, to a cranial cover including a base plate and a guide for holding a catheter after ultrasound guided cerebral shunt placement.

Hydrocephalus, otherwise known as "water on the brain", is a condition in which the ventricles of the brain, which typically maintains a steady balance of daily production and reabsorption of cerebrospinal fluid (CSF), fail and an excess amount of CSF accumulates. Various, either chronic or acute, conditions may cause this condition due to a lack of sufficient drainage. Known treatment of hydrocephalus may include placing a shunt into a ventricle to drain the excess fluid.

Recent treatment methods may utilize ultrasound visualization, a real-time imaging system, to increase the accuracy of shunt placement. In a typical procedure, shunt placement is achieved by drilling a relatively large diameter (e.g. 12 mm) burr hole into the skull and grinding away extra bone in one area to provide clearance for the catheter to be guided along the ultrasound device. Further complications may develop if this device is not accurately placed, including leakage around the catheter, hemorrhaging, migration of the catheter, and/or infection.

Two of the largest problems observed with cerebral shunt placement is shunt 1) obstruction which can be seen from catheter migration, and 2) infection which can be seen from pseudomeningocele formation at the burr hole site. Currently, there are no known cranial covers configured to both cover the burr hole, and firmly hold a catheter in a desired orientation.

Complications due to shunt placement can arise that are largely contributed to ultrasound guidance techniques. For example, infections may be partly due to the larger burr hole required to place the ultrasound device on the dura mater underneath the bone. In order to help prevent infection, a cranial plate would be able to cover the hole and decrease the exchange of fluids from the brain with the surrounding tissue. By developing a plate to cover the burr hole, the shunt infection rate in patients can be decreased, thus decreasing hospital visits, postoperative complications, and the number of shunt revision surgeries.

In certain patients with ultrasound guided cerebral shunt placements, pseudomeningocele (an abnormal collection of CSF around the brain) occurs, with some cases having the collection of fluid protrude out of the surface of the skull. This complication could be directly solved with the installation of a plate to prevent the fluid sack from protruding out. Along with preventing protrusions, the plate will act like a barrier preventing any external objects from entering the burr hole.

According to an illustrative embodiment of the present disclosure, a cranial cover is configured to be secured to a skull, and to cooperate with a catheter extending within a burr hole formed within the skull. The cranial cover includes a base plate having an upper surface, a lower surface, and an opening extending through the base plate between the upper surface and the lower surface. A guide extends upwardly from the upper surface of the base plate and includes a first riser, a second riser, and a receiver defined between the first riser and the second riser. A holder is supported by the first riser and the second riser and is configured to retain a distal portion of the catheter within the receiver and extending parallel to the upper surface of the base plate. A support boss extends downwardly from the lower surface of the base plate and is configured to be received within the burr hole.

According to another illustrative embodiment of the present disclosure, a ventricular catheter assembly includes a proximal catheter configured to be in fluid communication with a ventricle of a brain and to extend through a burr hole formed within a skull receiving the brain. A cranial cover cooperates with the proximal catheter. The cranial cover includes a base plate having an upper surface, a lower surface, and an opening extending through the base plate between the upper surface and the lower surface. A guide extends upwardly from the upper surface of the base plate and receives the proximal catheter for extending parallel to the upper surface of the base plate. The guide maintains the catheter angle entering the skull and reduces catheter migration.

According to a further illustrative embodiment of the present disclosure, a method of treating hydrocephalus includes the steps of forming a burr hole within the skull of a person, placing a proximal catheter in fluid communication with a ventricle of a brain within the skull, and positioning a cranial cover external to the skull. The cranial cover includes a base plate having an opening, and a guide supported by the base plate. The method further includes the steps of the aligning of the opening of the base plate with the burr hole in the skull, securing the base plate of the cranial cover to the skull, positioning the proximal catheter within the guide parallel to an outer surface of the skull, and securing the proximal catheter within the guide.

In certain illustrative embodiments of the present disclosure, the base plate may be produced in different materials allowing for either permanent placement or temporary placement (e.g., resorbable).

Additional features and advantages of the present invention will become apparent to those skilled in the art upon consideration of the following detailed description of the illustrative embodiments exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments elected for description have been chosen to enable one skilled in the art to practice the invention.

Figure 1:
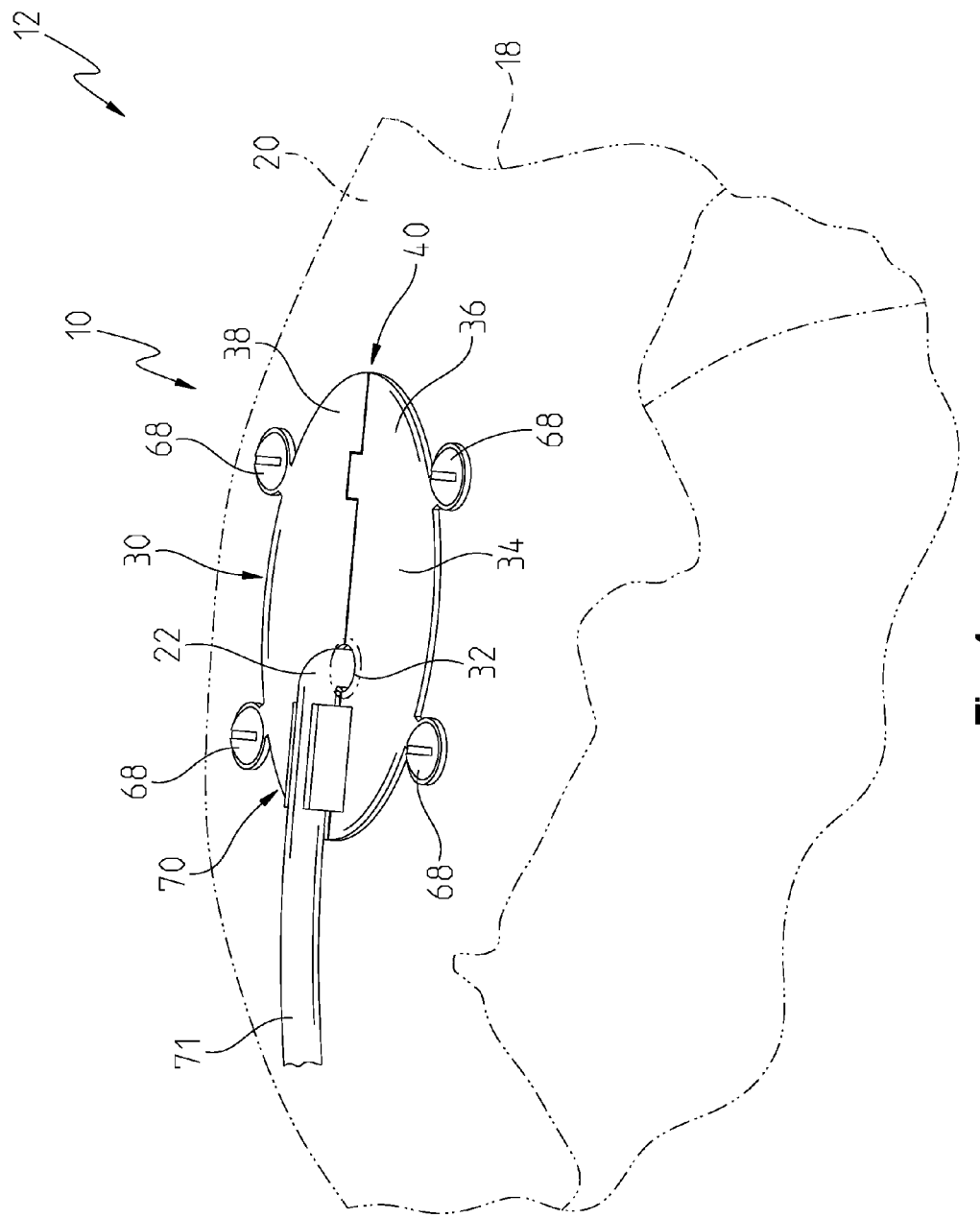
FIG. 1 is a perspective view of a ventricular catheter assembly including an illustrative cranial cover of the present disclosure installed on the skull of a person.
Figure 2:
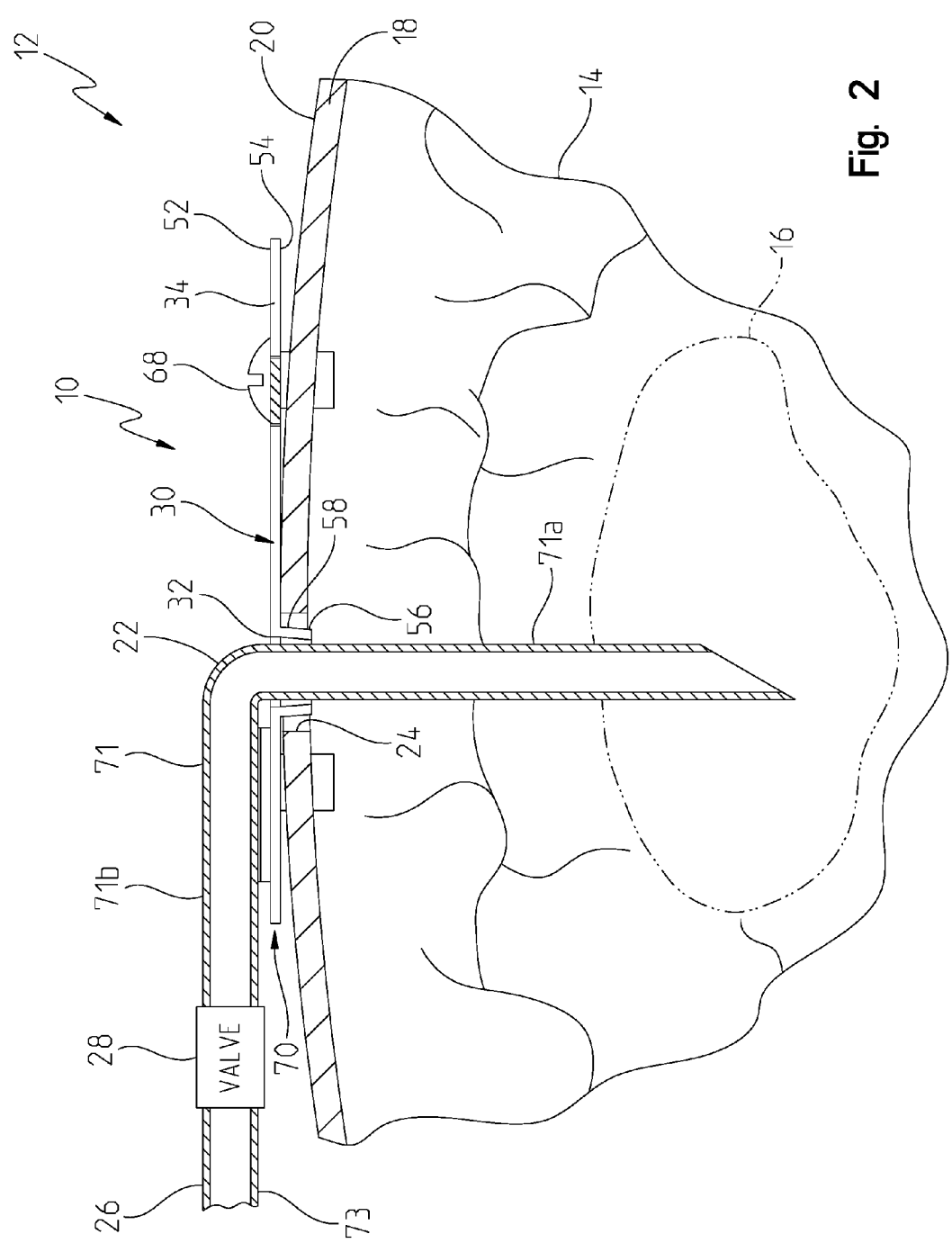
FIG. 2 is a cross-sectional view of the ventricular catheter assembly of FIG. 1.

With reference initially to FIGS. 1 and 2, a ventricular catheter assembly 10 is shown for use with a human person 12. More particularly, the ventricular catheter assembly 10 defines a cerebral shunt cooperating with a brain 14 by relieving fluid pressure from within a ventricle 16 of the brain 14. The ventricular catheter assembly 10 is illustratively secured to bone 18 of a skull 20.

The ventricular catheter assembly 10 illustratively includes a proximal catheter 22 in fluid communication with ventricle 16 of brain 14. As further detailed herein, a burr hole 24 is formed within the skull 20 of the person 12, such that the proximal catheter 22 extends outwardly from the ventricle 16 through the burr hole 24. A distal catheter 26 may be fluidly coupled to the proximal catheter 22 via a one way or a check valve 28. The valve 28 is fluidly coupled between the proximal catheter 22 and the distal catheter 26 to permit fluid flow only in a direction away from the ventricle 16. More particularly, cerebrospinal fluid (CSF) is permitted to flow out from ventricle 16 through the proximal catheter 22, the valve 28, and the distal catheter 26.

With further reference to FIGS. 1 and 2, an illustrative cranial cover 30 is positioned external to the skull 20 and includes an opening 32 to receive the proximal catheter 22 in alignment with the burr hole 24. Various illustrative embodiments of the cranial cover 30, 130, 230 and 330 are further shown in FIGS. 3-8.

Figure 3:
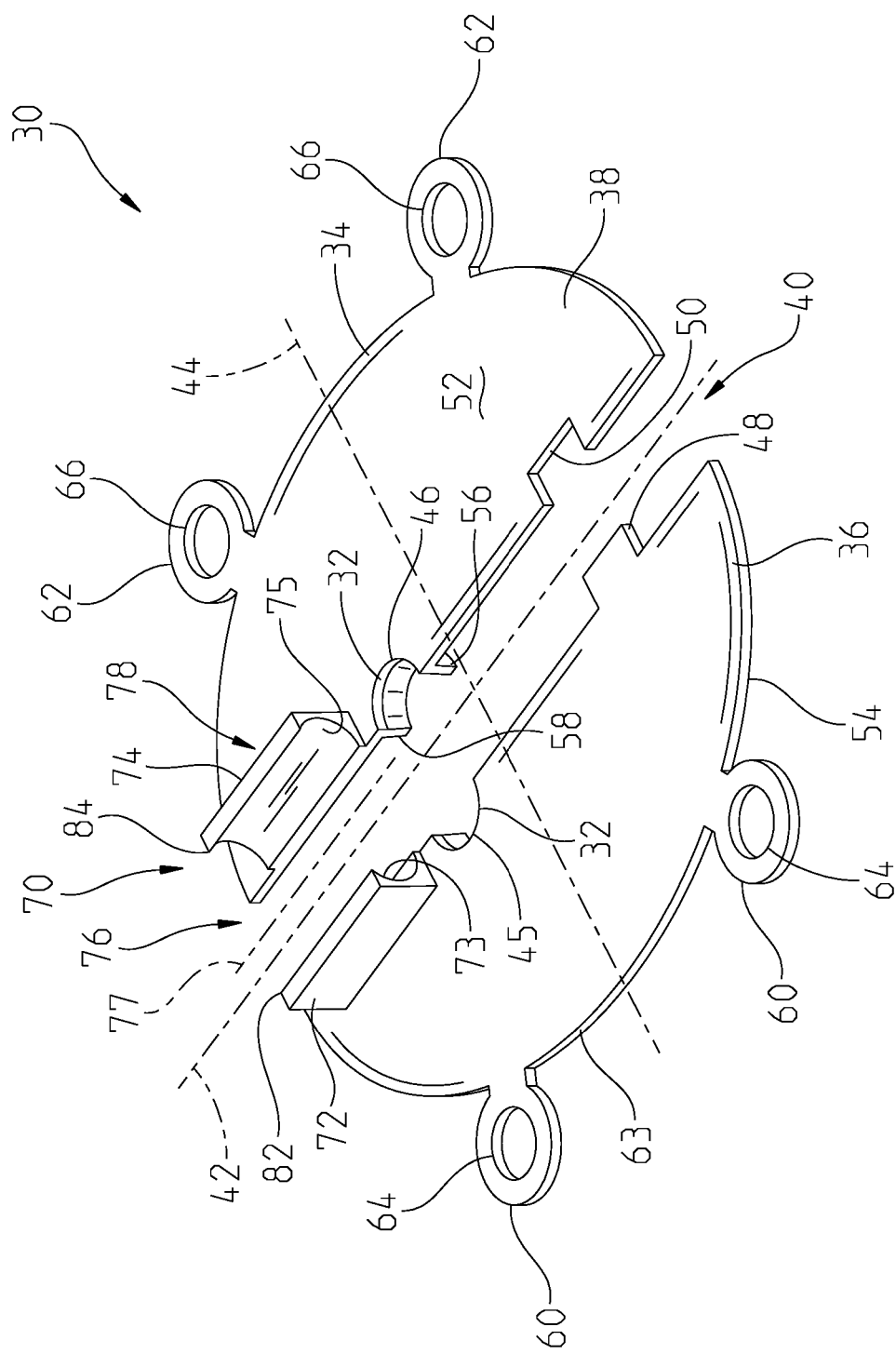
FIG. 3 is a perspective view of the illustrative cranial cover of FIG. 1, the cranial cover including a base plate and a guide separated along a longitudinal split interface.

As shown in FIGS. 1-3, illustrative cranial cover 30 includes an oval shaped base plate 34, including a first member 36 and a second member 38. The oval shaped base plate 34 facilitates full coverage over the burr hole 24, while minimizing catheter migration and preventing pseudo-meningoceles. The second member 38 of the base plate 34 is separable from the first member 36 of the base plate 34 along a split interface 40. Illustratively, the base plate 34 has a length (along a major or longitudinal axis 42) of approximately 22 millimeters, and a width (along a minor or lateral axis 44) of approximately 17 millimeters. In the illustrative embodiment of FIG. 3, the split interface 40 extends longitudinally along the major axis 42 of the base plate 34. The split interface 40 illustratively extends through opening 32 thereby defining a first semi-circular notch 45 in the first member 36 and a second semi-circular notch 46 in the second member 38. Illustratively, each notch 44 and 46 has a radius of approximately 1.25 millimeters, such that the opening 32 has a diameter of approximately 2.5 millimeters.

An alignment tab 48 may be supported by the first member 36 at the split interface 40, while an alignment notch 50 may be supported by the second member 38 at the split interface 40. The alignment tab 48 may be received within the alignment notch 50 to facilitate proper orientation and alignment of the first member 36 relative to the second member 38. In certain illustrative embodiments, a locking device (e.g., a tongue snap-fit into a groove) may be supported at the split interface 40 to couple or lock together the first member 36 and the second member 38.

The illustrative base plate 34 includes an upper surface 52 and a lower surface 54. The opening 32 is illustratively a thru-hole extending between the upper surface 46 and the lower surface 48 of the base plate 34. In certain illustrative embodiments, the opening 32 may be slightly oval shaped thereby allowing for slight movement of the proximal catheter 22 while being installed.

A support boss 56 extends downwardly from the lower surface 48 of the base plate 34 and into the burr hole. Illustratively, the support boss 56 is centered around the opening 32 and provides extra support to the proximal catheter 22 extending through the burr hole 24 while preventing migration of the catheter 22. The support boss 56 may include a cylindrical side wall 58, separated along the interface 40, and extending downwardly from the lower surface 54 of the base plate 34 by approximately 3 millimeters.

Mounting tabs 60 and 62 may extend outwardly from an outer edge 63 of the base plate 34. Illustratively, a first pair of mounting tabs 60 extend outwardly from the first member 36 and a second pair of mounting tabs 62 extend outwardly from the second member 38. It should be appreciated that the location and number of mounting tabs 60 and 62 may vary. Each mounting tab 60, 62 includes an opening 64, 66 to receive a bone screw 68 to secure the base plate 34 to bone 18 of the skull 20. Illustratively, the base plate 34 is resilient or flexible such that it may conform to the outer curvature of the skull 20 when secured thereto via the bone screws 68.

The base plate 34 may be formed of different materials based upon, for example, permanent or temporary placement. In one illustrative embodiment for permanent placement, the base plate 34 is formed of titanium and has a thickness of approximately 0.5 millimeters. Titanium provides sufficient strength and protection to the brain 14 by covering the burr hole 24. However, various other materials, including plastics and composites suitable for medical use may be substituted for titanium. In certain illustrative embodiments for temporary placement, the base plate 34 may be formed of a resorbable material.

A catheter guide 70 extends upwardly from the upper surface 52 of the base plate 34 and is configured to receive and hold the proximal catheter 22. The proximal catheter 22 and the distal catheter 26 include tubes 71 and 73, respectively, to convey fluid (e.g., cerebrospinal fluid) from the ventricle 16 of the brain 14. Tube 71 of the proximal catheter 22 illustratively includes a first or proximal portion 71a extending substantially perpendicular to the outer surface of the skull 20 and the lower surface 54 of the base plate 34, and a second portion 71b extending substantially perpendicular to the first portion 71a and substantially parallel to the outer surface of the skull 20 and the upper surface 52 of the base plate 34.

As shown in FIG. 3, the guide 70 illustratively includes opposing first and second arms or risers 72 and 74 extending upwardly from the upper surface 52 of the base plate 34. A receiver 76 is defined between the first and second risers 72 and 74 for receiving second portion 71b of the tube 71 of the proximal catheter 18. More particularly, arcuate inner surfaces 73 and 75 of the risers 72 and 74 illustratively define cylindrical receiver 76. In the illustrative embodiment, the receiver 76 defines a receiver axis 77 which extends parallel to the major axis 42 of the base plate 34. Illustratively, the first riser 72 is supported by the first member 36 of the base plate 34, and the second riser 74 is supported by the second member 38 of the base plate 34.

A holder 78 is supported by the first and second risers 72 and 74, and illustratively includes inwardly extending first and second lips 82 and 84. The first and second lips 82 and 84 may snap-fit over the tube 71 to retain the proximal catheter 18 in place, such that the distal portion 71b extends substantially parallel to the upper surface 52 of the base plate 34.

Installation of the ventricular catheter 10 including cranial cover 30 is further detailed below. It should be appreciated that installation of cranial cover 30' is substantially the same as with cranial cover 30. During installation, burr hole 24 is initially formed within the skull 20. Illustratively, the burr hole 24 has a diameter (e.g., approximately 12 millimeters) sufficient to receive a conventional ultrasound device or probe (not shown). The ultrasound device serves as a guide for the placement of the proximal catheter 22 into the ventricle 16. Illustratively, the burr hole 24 is formed by drilling a pilot hole and then grinding away excess bone 18 to provide clearance for the proximal catheter 22 to be guided along the ultrasound device. The proximal portion 71a of the tube 71 is inserted into the ventricle 16 such that the proximal catheter 22 is in fluid communication with the ventricle 16.

Either before or after insertion of the proximal catheter 22, the first member 36 of the base plate 34 is illustratively secured to the skull 20 through bone screws 68. The proximal portion 71a of the catheter tube 71 is received within the semi-circular notch 45 of the first member 36. The second member 38 of the base plate 34 is then aligned along the interface 40 with the first member 36, with the catheter tube 71 being received between the second semi-spherical notch 46 and the first semi-spherical notch 45. Illustratively, the alignment tab 48 is received within the alignment notch 50 to properly orient and align the first and second members 36 and 38 of the base plate 34. The second member 38 is then secured to the skull 20 through the bone screws 68. The base plate 34 may be aligned with the burr hole 24 by positioning the support boss 56 within the burr hole 24 of the skull 20.

The proximal catheter 22 is also received within the guide 70. More particularly, the distal portion 71b of the catheter tube 71 is positioned within the receiver 76 defined between the first and second risers 72 and 74. The retaining lips 82 and 84 secure the catheter tube 71 in position. The tube 71 bends 90 degrees as it exits the skull 20 and extends above the base plate 34, such that the distal portion 71b of the tube 71 extends substantially perpendicular to the outer surface of the skull 20 and the upper surface 52 of the base plate 34.

Figure 4:
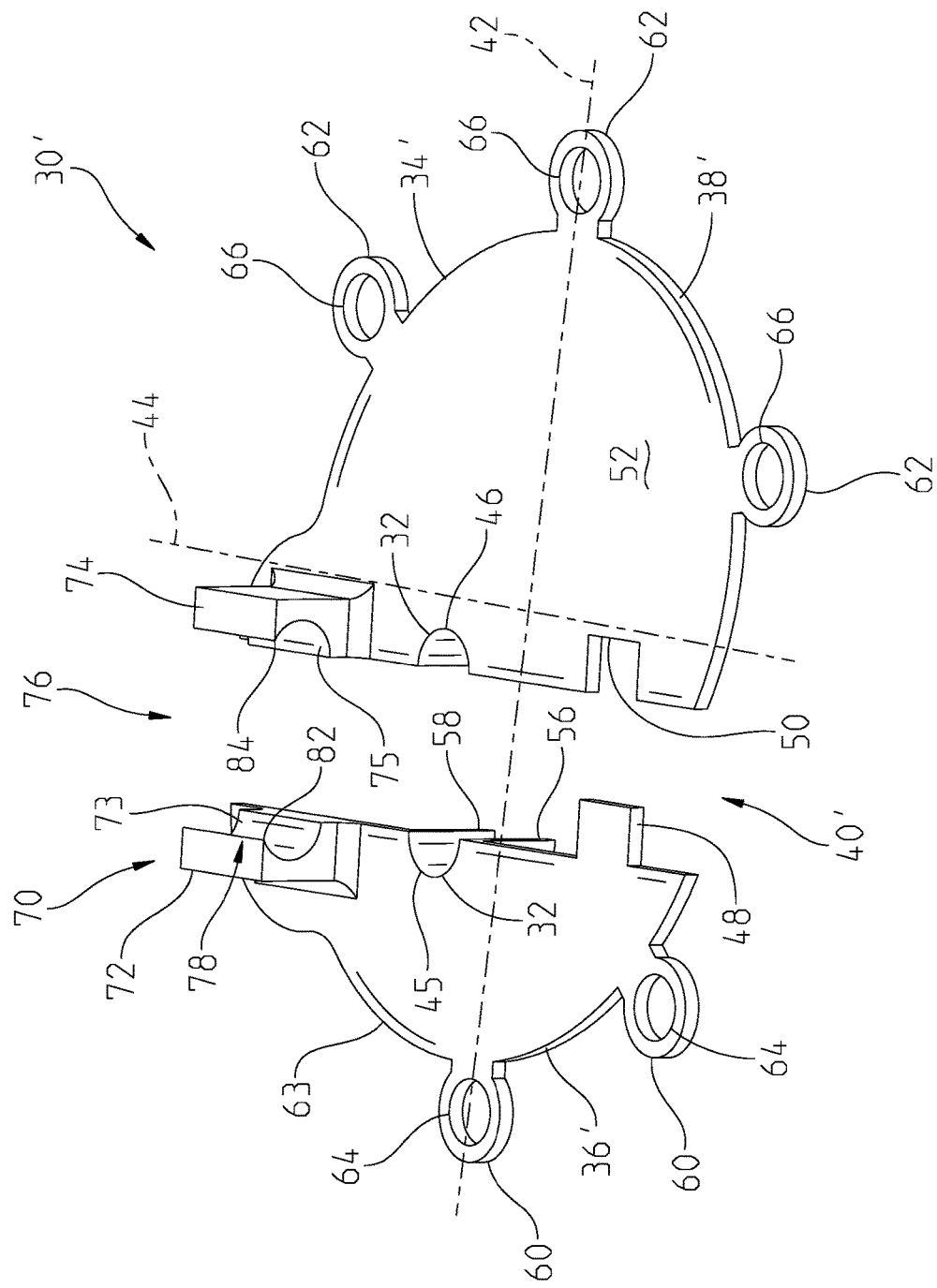
FIG. 4 is a further illustrative embodiment cranial cover including a base plate and a guide separated along a lateral split interface.

FIG. 4 shows a further illustrative cranial cover 30' including a base plate 34' separated along a lateral split interface 40'. The cranial cover 30' is substantially similar to the cranial cover 30, but with the lateral split interface 40' extending substantially perpendicular to the longitudinal split interface 40. As such, similar components between cranial covers 30 and 30' are identified with like reference numbers. It should be appreciated that the split interface 40, 40' may be positioned at any location or orientation between first and second members 36, 36' and 38, 38' based upon structure of the skull 20 and the brain 14, and surgical preferences.

Figure 5:
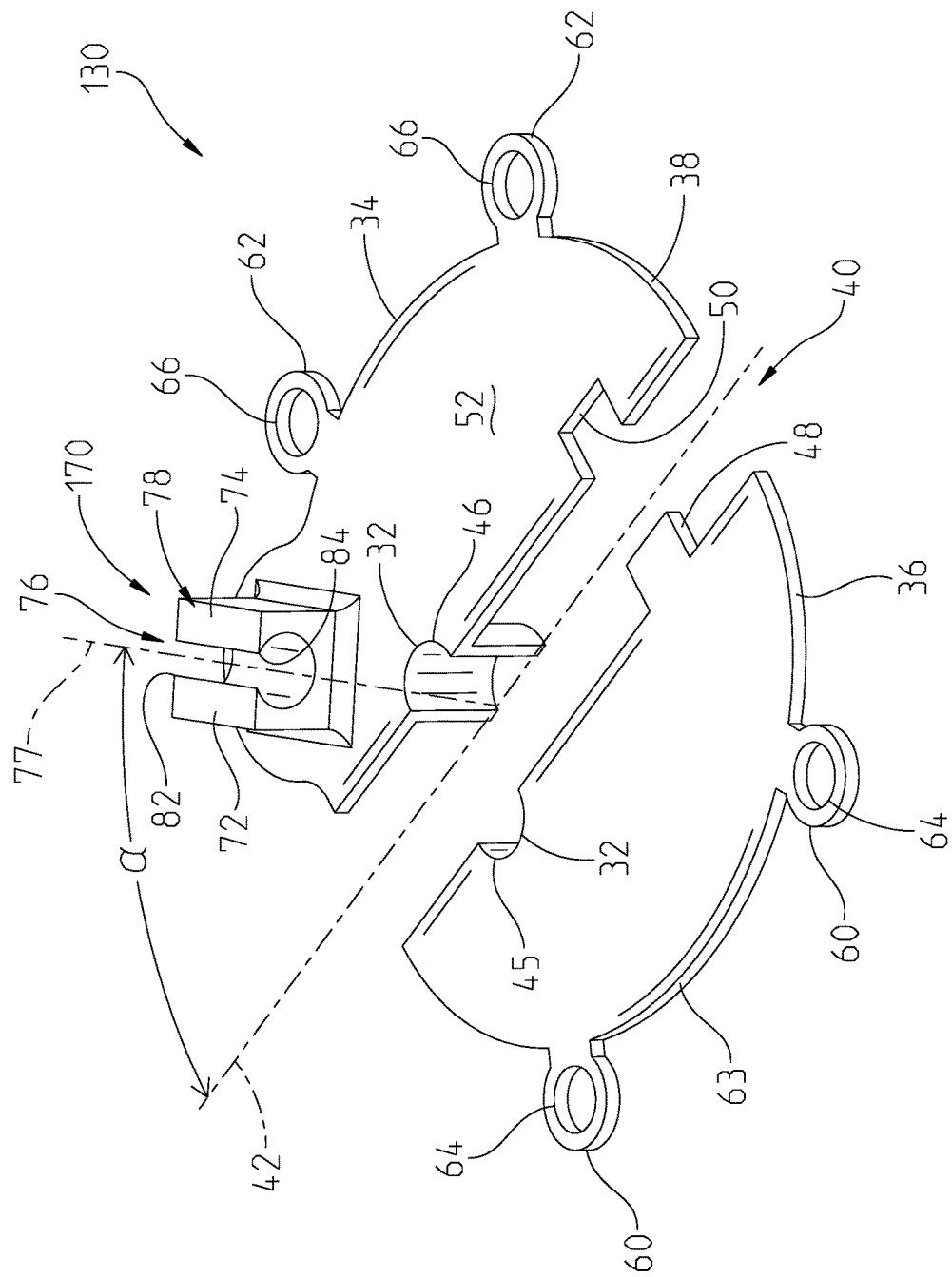
FIG. 5 is a further illustrative embodiment cranial cover including a base plate separated along a longitudinal split interface.
Figure 6:
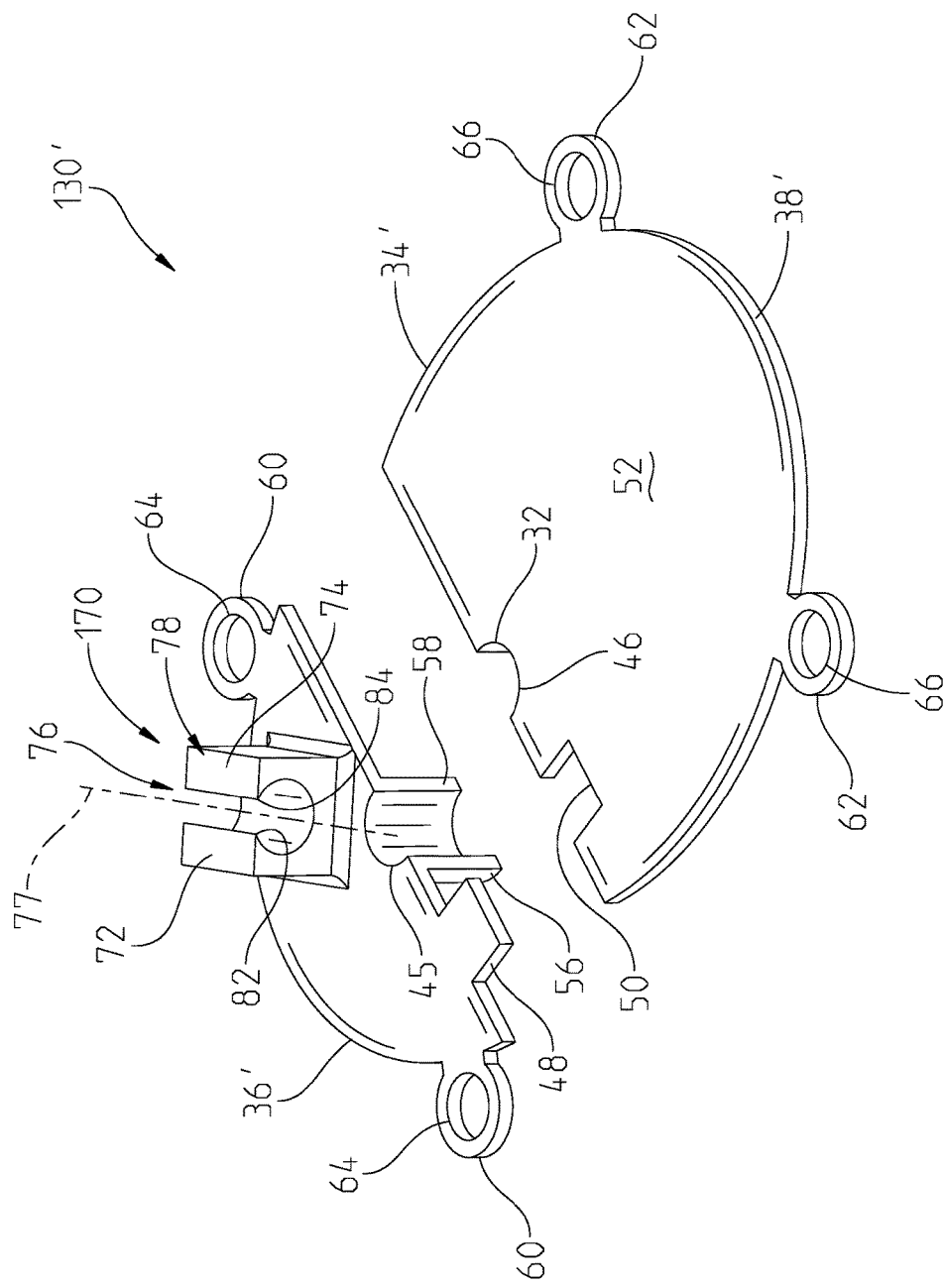
FIG. 6 is a further illustrative embodiment of the cranial cover including a base plate separated along a lateral split interface.

FIGS. 5 and 6 illustrate further cranial covers 130 and 130' that include many similar components to those detailed above in connection with cranial covers 30 and 30'. As such, similar components are identified with like reference numbers. For example, the cranial cover 130 includes base plate 34, and the cranial cover 130' includes base plate 34'.

A catheter guide 170, 170' is supported by each base plate 34, 34'. More particularly, the guide 170 is supported by the second member 38 of base plate 34, and the guide 170' is supported by the first member 36' of base plate 34'. The guide 170 may be pre-threaded and secured within an opening formed within the respective member 38, 36' of the base plate 34, 34'. With reference to FIG. 5, the receiver axis 77 of the guide 170 may be oriented at a variety of different angles α relative to the longitudinal axis 42. For example, the angle α illustratively may be between 45 and 90 degrees.

During installation of the cranial cover 130, the first member 36 of the base plate 34 is illustratively secured to the skull 20 during placement of the proximal catheter 22 within the brain 14. The second member 38 of the base plate 34 is then secured to the skull 20 after the proximal catheter 22 is positioned within the semi-circular openings 45 and 46. The distal portion 71b of catheter tube 71 may then be received (e.g., snap-fit) within the receiver 76 of the holder 170. Installation of the cranial cover 130' is substantially similar to that of cranial cover 130.

Figure 7:
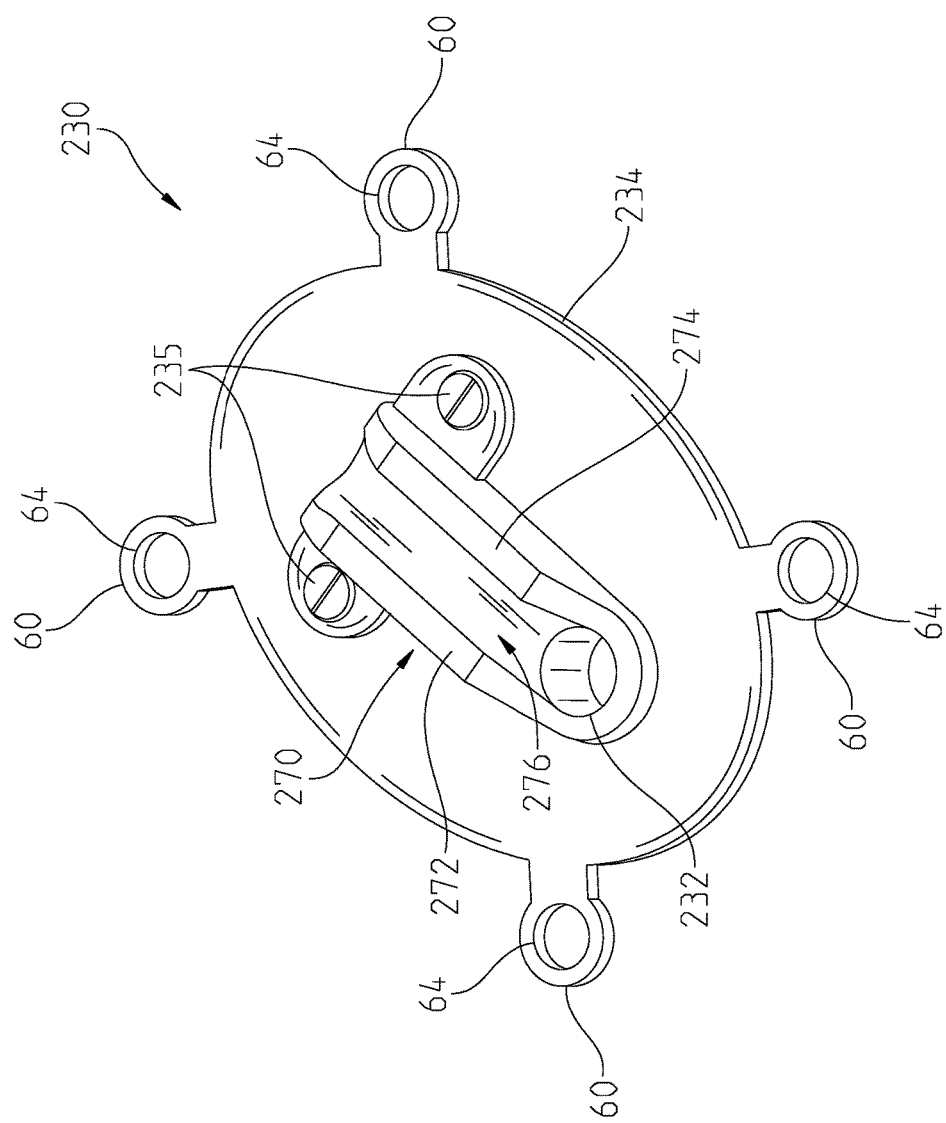
FIG. 7 is a perspective view of another illustrative cranial cover including a guide fixed to a base plate.

With reference now to FIG. 7, a further illustrative cranial cover 230 includes a base plate 234 having an opening used for the placement of a right angle guide 270. Cranial cover 230 may use a conventional right angle guide 270 which is secured to the cranial plate 234 through conventional fasteners, such as snap-fit connectors 235. The guide 270 illustratively includes an opening 232 to receive the proximal portion 71a of the catheter 22, and risers 272 and 274 defining a receiver 276 for receiving distal portion 71b of the catheter 22. The cranial plate 234 and the right angle guide 270 may be pre-threaded onto the proximal catheter 22. After the proximal catheter 22 is properly inserted into the brain 14, the cranial plate 234 and the right angle guide 270 are then slid down the catheter 22 until the plate 234 is flush with the skull 20, at which time it may be secured into place using bone screws 68 extending through openings 64 in mounting tabs 60.

Figure 8:
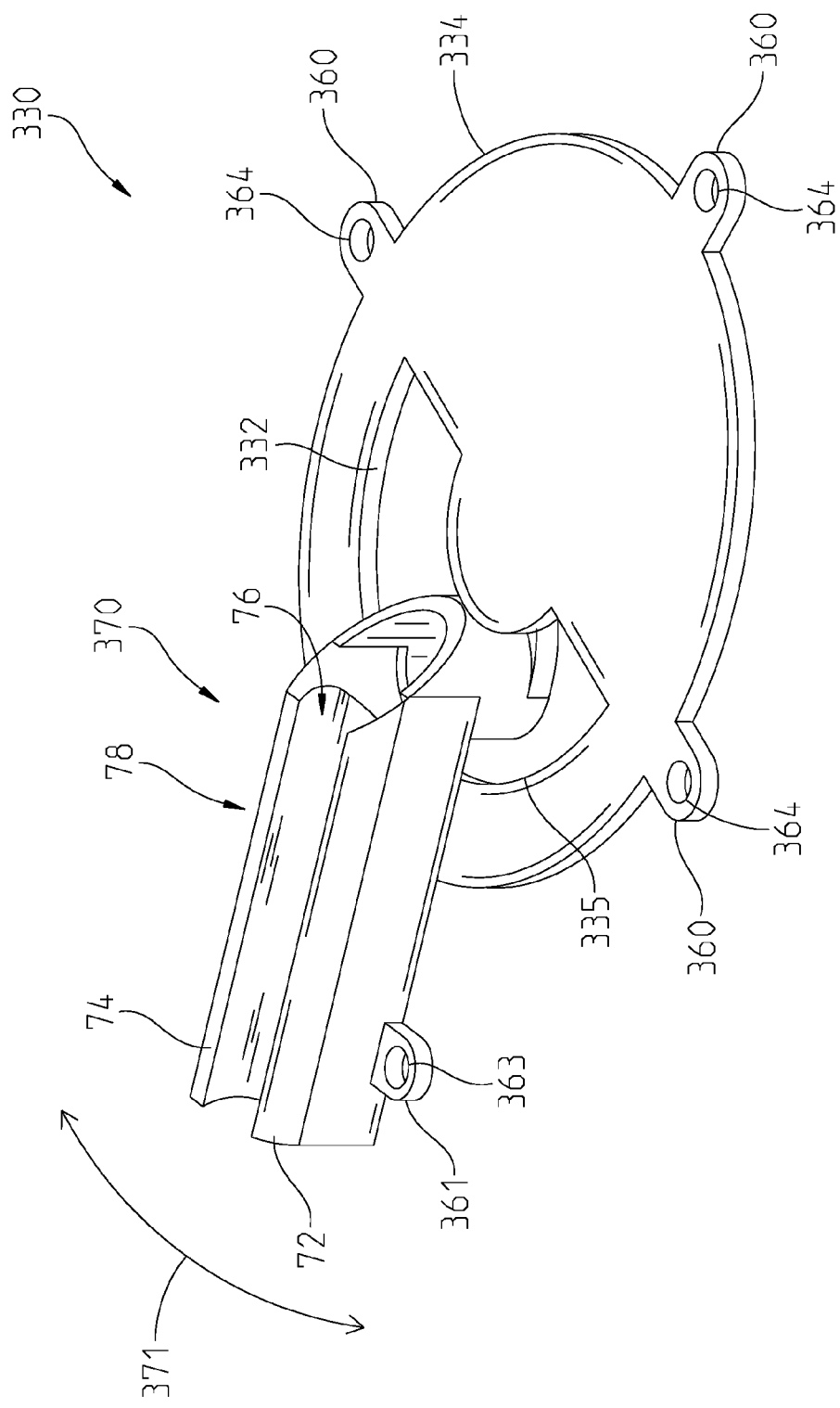
FIG. 8 is a perspective view of a further illustrative cranial cover of the present disclosure including a guide supported for movement along an arcuate track formed within a base plate.

With reference to FIG. 8, a cranial cover 330 illustratively includes a right angle guide 370 supported for movement relative to a base plate 334. The right angle guide 370 is configured to move in the direction of arrows 371 (e.g., swivel) along an arcuate track 335 defined by opening 332 in the cranial plate 334, thereby allowing for optimal customization of catheter placement. Mounting tabs 360 include openings 364 for receiving bone screws 68 to secure the base plate 334 to the skull 20. The right angle guide 370 illustratively includes mounting tabs 361 having openings 363 to receive bone screws 68 for securing the guide 370 to the skull 20. The cranial plate 334 and the right angle guide 370 may then be secured to the skull 20, over the burr hole 24, after the catheter 22 had been inserted.

Although the invention has been described in detailed with reference to preferred embodiments, variations and modifications exist within the spirit and scope of the invention as described and defined in the following claims.

The invention claimed is:
1. A cranial cover configured to be secured to a skull, and to cooperate with a catheter extending within a burr hole formed within the skull, the cranial cover comprising:
  a base plate including an upper surface, a lower surface, and an opening extending through the base plate between the upper surface and the lower surface;

a guide extending upwardly from the upper surface of the base plate, the guide including a first riser, a second riser, a receiver defined between the first riser and the second riser, and a holder supported by the first riser and the second riser and configured to retain a distal portion of the catheter extending within the receiver and parallel to the upper surface of the base plate; and a support boss extending downwardly from the lower surface of the base plate and configured to be received within the burr hole.

2. The cranial cover of claim 1, wherein the base plate includes a first member, a second member, and a split interface extending through the opening between the first member and the second member.

3. The cranial cover of claim 2, wherein the guide is longitudinally aligned along the split interface of the base plate, the first riser is supported by the first member of the base plate, and the second riser is supported by the second member of the base plate.

4. The cranial cover of claim 2, wherein the first member of the base plate includes an alignment tab, and the second member of the base plate includes an alignment notch for receiving the alignment tab.

5. The cranial cover of claim 1, further comprising a plurality of mounting tabs extending outwardly from the base plate, and a plurality of bone screws received within the mounting tabs for securing the base plate to the skull.

6. The cranial cover of claim 1, wherein the opening within the base plate includes an arcuate track, and the guide is received within the arcuate track for movement along an arc.

7. The cranial cover of claim 1, wherein the holder includes first and second lips supported by the first and second risers, the first and second lips configured to retain the distal portion of the catheter between the first and second risers.

8. The cranial cover of claim 1, wherein the base plate is resilient to conform to curvature of the skull.

* * * * *